US010980680B1

(12) United States Patent
Lee (10) Patent No.: US 10,980,680 B1
(45) Date of Patent: Apr. 20, 2021

(54) SANITARY PAD

(71) Applicant: JK INSPIR., Seoul (KR)

(72) Inventor: Hwa Jin Lee, Seongnam-si (KR)

(73) Assignee: JK INSPIR, Seoul (KR)

( * ) Notice: Subject to any disclaimer, the term of this patent is extended or adjusted under 35 U.S.C. 154(b) by 0 days.

(21) Appl. No.: 16/859,115

(22) Filed: Apr. 27, 2020

(30) Foreign Application Priority Data

Dec. 24, 2019 (KR) .......................... 10-2019-0173602

(51) Int. Cl.
| A61F 13/511 | (2006.01) |
| A61F 13/15 | (2006.01) |
| A61F 13/53 | (2006.01) |
| A61F 13/532 | (2006.01) |
| A61F 13/475 | (2006.01) |

(52) U.S. Cl.
CPC ...... *A61F 13/532* (2013.01); *A61F 13/15577* (2013.01); *A61F 13/475* (2013.01); *A61F 13/51121* (2013.01); *A61F 2013/1539* (2013.01); *A61F 2013/15552* (2013.01); *A61F 2013/530029* (2013.01)

(58) Field of Classification Search
CPC ............ A61F 2013/1539; A61F 13/474; A61F 13/532; A61F 13/475; A61F 13/15577; A61F 13/51121
See application file for complete search history.

(56) References Cited

U.S. PATENT DOCUMENTS

| 4,596,570 A | * | 6/1986 | Jackson | A61F 13/4704 |
| | | | | 604/387 |
| 2010/0076392 A1 | * | 3/2010 | Kudo | A61F 13/4704 |
| | | | | 604/385.01 |
| 2011/0071486 A1 | | 3/2011 | Harada et al. | |
| 2015/0164704 A1 | * | 6/2015 | Chae | A61F 13/4704 |
| | | | | 604/385.03 |
| 2017/0239102 A1 | * | 8/2017 | Lee | A61F 13/5611 |
| 2018/0193205 A1 | * | 7/2018 | Beck | A61F 13/15211 |
| 2019/0099303 A1 | * | 4/2019 | Viens | A61F 13/55185 |

FOREIGN PATENT DOCUMENTS

| JP | 2004-298411 A | 10/2004 |
| JP | 2009-240643 A | 10/2009 |
| KR | 20-0196072 Y1 | 9/2000 |
| KR | 20-0276953 Y1 | 5/2002 |

(Continued)

OTHER PUBLICATIONS

Korean Grant of Patent for KR 10-2019-0173602 date Feb. 26, 2020.

(Continued)

*Primary Examiner* — Tatyana Zalukaeva
*Assistant Examiner* — Jessica R Arble
(74) *Attorney, Agent, or Firm* — Sughrue Mion, PLLC (57) ABSTRACT

The present invention provides a sanitary pad including an upper sheet made of pure organic cotton through which a liquid is permeable, a first absorbing sheet disposed below the upper sheet and made of pure organic cotton configured to absorb the liquid, a second absorbing sheet disposed below the first absorbing sheet and made of natural compressed pulp configured to absorb the liquid, and a waterproof sheet disposed below the second absorbing sheet and having air permeability.

3 Claims, 7 Drawing Sheets

(56) References Cited

FOREIGN PATENT DOCUMENTS

| KR | 10-2005-0080166 A | 8/2005 |
| KR | 10-2007-0048691 A | 5/2007 |
| KR | 10-2012-0108183 A | 10/2012 |
| KR | 10-1385620 B1 | 4/2014 |
| KR | 10-1470249 B1 | 12/2014 |
| KR | 10-1879280 B1 | 8/2018 |
| KR | 10-2014032 B1 | 10/2019 |

OTHER PUBLICATIONS

Korean Notice of Refusal for 10-2019-0173602 dated Jan. 18, 2020.
Gang InSuk Extrinsic; Dyeing. Gate Corp. Sep. 10, 2001, First Edition; pp. 34-45.

\* cited by examiner

SANITARY PAD

CROSS-REFERENCE TO RELATED APPLICATION

This application claims priority to and the benefit of Korean Patent Application No. 10-2019-0173602, filed on Dec. 24, 2019, the disclosure of which is incorporated herein by reference in its entirety.

BACKGROUND

1. Field of the Invention

The present invention relates to a sanitary pad.

2. Discussion of Related Art

Most women use a sanitary pad during menstruation by attaching the sanitary pad inside their underwear. To absorb menstrual fluid, the sanitary pad is formed of compressed cotton and a solid substance, which are made of natural materials, and a non-woven fabric surface, which includes the compressed cotton and the solid substance therein and has functions of reinforcing menstrual fluid absorption rate and preventing leakage of menstrual fluid.

However, numerous chemicals are used in making a sanitary pad. A menstrual fluid absorption cover of the sanitary pad is polyvinyl-based, and cotton in the sanitary pad contains absorption gel, such as polyacrylate, which is a chemical in a granular form. Polyacrylate is a chemical substance that is inexpensive and easy to manufacture, and thus it is utilized in various ways.

Hundreds of thousands of tons of polyacrylate are consumed annually as a superabsorbent material for disposable sanitary pads and the like. However, there is a problem in that, because polyacrylate is not biodegradable and does not rot over time, a huge amount of polyacrylate disposed of in a landfill causes environmental pollution. Further, the chemicals may cause fever, skin maceration, itching, and the like.

To partially address such problems, the top layer of the sanitary pad is made of a certain kind of cotton. However, because the sanitary pad basically contains superabsorbent polymer therein, there may be a problem such as introduction of chemical substances into the female body when the sanitary pad is used for a long period of time.

RELATED ART DOCUMENT

Korean Utility Model Registration No. 20-0196072 (Jul. 4, 2000)

SUMMARY OF THE INVENTION

Embodiments of the present invention are directed to providing an eco-friendly sanitary pad that uses pure organic cotton and natural compressed pulp without using superabsorbent polymer.

Embodiments of the present invention are also directed to providing a sanitary pad that uses two absorbing sheets so that an absorption rate and an absorption capacity are improved.

Embodiments of the present invention are also directed to providing a sanitary pad that uses pure organic cotton to increase a cushion feeling and absorption rate and uses natural compressed pulp to increase absorption capacity.

Embodiments of the present invention are also directed to providing a sanitary pad that uses natural compressed pulp manufactured by a chlorine-free bleaching process.

Embodiments of the present invention are also directed to providing a sanitary pad that uses natural compressed pulp which is compressed only using water and heat without using an adhesive.

According to an embodiment of the present invention, there is provided a sanitary pad including an upper sheet made of pure organic cotton through which a liquid is permeable, a first absorbing sheet disposed below the upper sheet and made of pure organic cotton configured to absorb the liquid, a second absorbing sheet disposed below the first absorbing sheet and made of natural compressed pulp configured to absorb the liquid, and a waterproof sheet disposed below the second absorbing sheet and having air permeability.

The second absorbing sheet may be manufactured by a chlorine-free bleaching process.

The second absorbing sheet may be manufactured by a hydrogen peroxide bleaching process.

The upper sheet, the first absorbing sheet, and the second absorbing sheet may include a leakage preventing protrusion part formed to protrude from both sides in a longitudinal direction.

The sanitary pad may further include a length adjusting part disposed at a rear portion of an upper surface of the upper sheet, disposed to gradually protrude more in a rearward direction, and configured to press against buttocks of a user.

The length adjusting part may include a cover part, whose edge is removably connected to the upper sheet, and an absorbing part, which is disposed in a state of being folded a plurality of times at an inner side of the cover part and configured to, when a folded portion is unfolded, be unfolded toward an outer side of the rear portion of the upper sheet.

The first absorbing sheet may include a concave portion and the second absorbing sheet may include a convex portion, which is insertable into the concave portion, so that the concave portion and the convex portion press against each other as the first absorbing sheet and the second absorbing sheet expand due to absorption of a liquid.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, specific embodiments of the present invention will be described with reference to the accompanying drawings. However, the embodiments are merely illustrative, and the present invention is not limited thereto.

In describing the present invention, in a case in which detailed description of a known art relating to the present invention is determined as having the possibility of unnecessarily obscuring the gist of the present invention, the detailed description will be omitted. Also, terms used herein are those defined in consideration of functions in the present invention and may vary according to an intention, practice, and the like of a user or an operator. Therefore, the terms should be defined on the basis of content throughout the present specification.

The technical idea of the present invention is determined by the claims below. The following embodiments are merely means for efficiently describing the technical idea of the present invention to those of ordinary skill in the art to which the present invention pertains.

Figure 1:
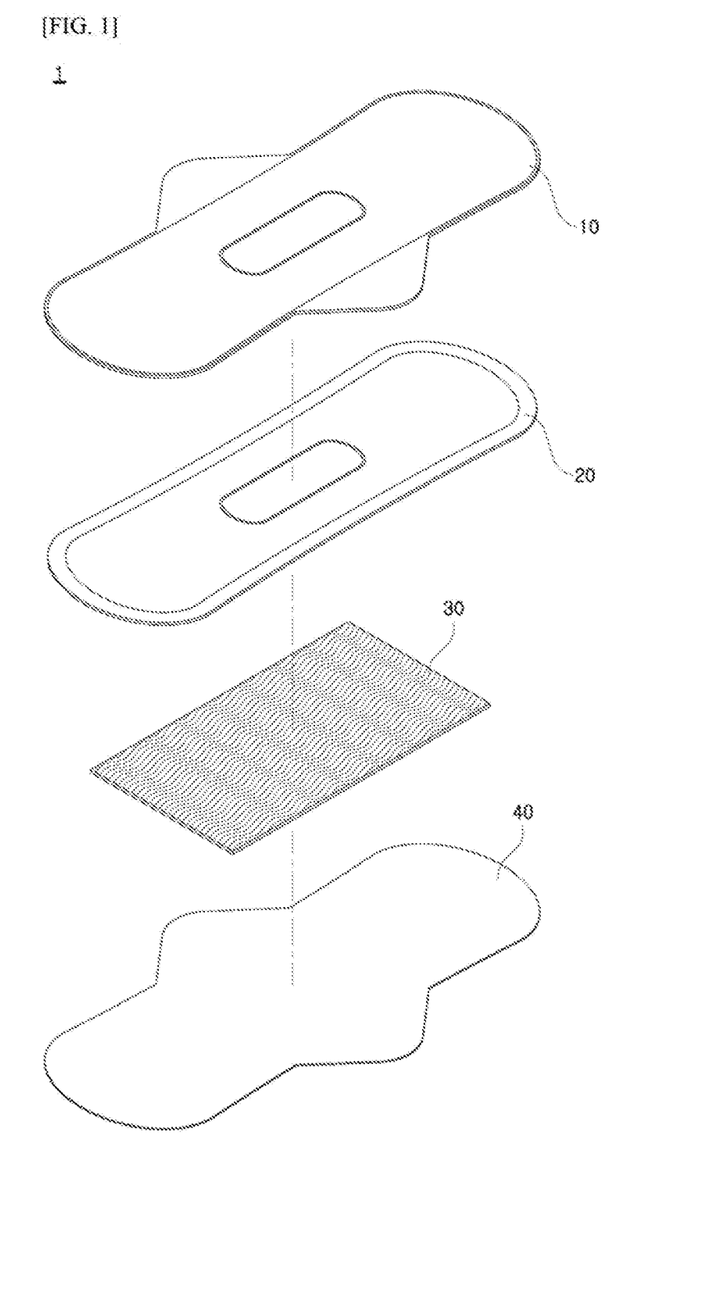
FIGS. 1 and 2 are views illustrating a sanitary pad according to an embodiment of the present invention.
Figure 2:
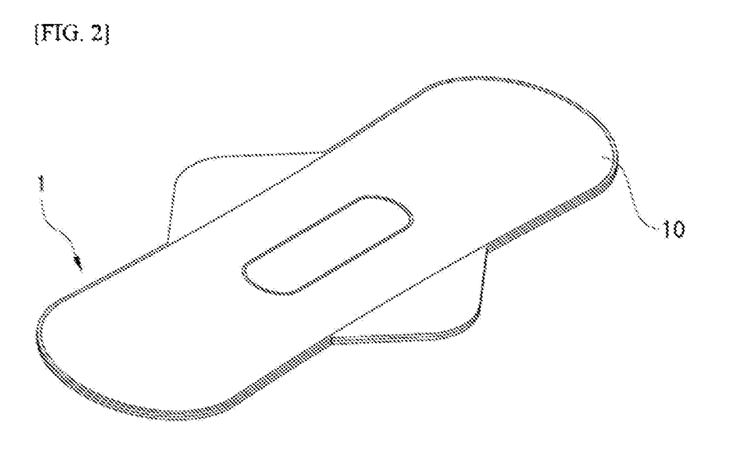

FIGS. 1 and 2 are views illustrating a sanitary pad 1 according to an embodiment of the present invention.

Referring to FIGS. 1 and 2, the sanitary pad 1 may include an upper sheet 10, a first absorbing sheet 20, a second absorbing sheet 30, and a waterproof sheet 40.

The upper sheet 10 is a layer coming into contact with a user's skin. The upper sheet 10 may be made of pure organic cotton through which a liquid is permeable. Although not illustrated in the drawings, a plurality of air holes may be formed in the upper sheet 10 and allow a liquid (that is, menstrual fluid) to be absorbed into the first absorbing sheet 20 and the second absorbing sheet 30.

Pure organic cotton is cotton grown through organic farming on healthy land on which large amounts of chemical fertilizers and defoliants, which are used for growing ordinary cotton, have not been used for three or more years. Thus, pure organic cotton may not cause irritation to the skin and have a soft and mild feeling. Unlike the cotton grown using chemical fertilizers and defoliants, pure organic cotton may have a soft and non-irritating feeling. In this way, because the upper sheet 10 is formed of a pure cotton cover, the user's skin may not be irritated even when the upper sheet 10 comes into contact with the user's skin.

The first absorbing sheet 20 may be disposed below the upper sheet 10 and may be made of pure organic cotton configured to absorb the liquid. The first absorbing sheet 20 is a layer that is the second closest to the skin after the upper sheet 10. The first absorbing sheet 20 may be made of pure organic cotton to prevent irritation to the user's skin.

The first absorbing sheet 20 made of pure organic cotton has a high instant absorption force and cushion feeling. The first absorbing sheet 20 may have a predetermined thickness larger than that of the upper sheet 10. The first absorbing sheet 20 may have a thickness that allows absorption of a predetermined amount of the liquid.

The second absorbing sheet 30 may be disposed below the first absorbing sheet 20 and may be made of natural compressed pulp configured to absorb the liquid. The second absorbing sheet 30 is made of natural compressed pulp which is compressed using only water and heat without using an adhesive.

Specifically, the second absorbing sheet 30 may be made of natural compressed pulp. Because the second absorbing sheet 30 made of natural compressed pulp has high absorption capacity, it may complement an insufficient absorption capacity of pure cotton. Also, the natural compressed pulp of the second absorbing sheet 30 may be manufactured by a chlorine-free bleaching process. For example, the second absorbing sheet 30 may be manufactured by a hydrogen peroxide bleaching process.

In a case in which the second absorbing sheet 30 is manufactured by the hydrogen peroxide bleaching process, because hydrogen peroxide does not react with wood cellulose, the amount of water used may be reduced when producing the natural compressed pulp. Also, unlike chlorine bleaching, hydrogen peroxide bleaching may reduce discharge of wastewater for washing.

In this way, by absorbing menstrual fluid using the first absorbing sheet 20 made of pure organic cotton and the second absorbing sheet 30 made of natural compressed pulp, which are arranged in a double layer, without using a chemical absorber, it is possible to eliminate side effects due to the chemical absorber and increase an absorption capacity due to the first absorbing sheet 20 and the second absorbing sheet 30 arranged in a double layer.

The waterproof sheet 40 may be disposed below the second absorbing sheet 30 and made of a waterproof material having air permeability. The waterproof sheet 40 may prevent leakage of the liquid to the outside at the lowermost layer.

Figure 3:
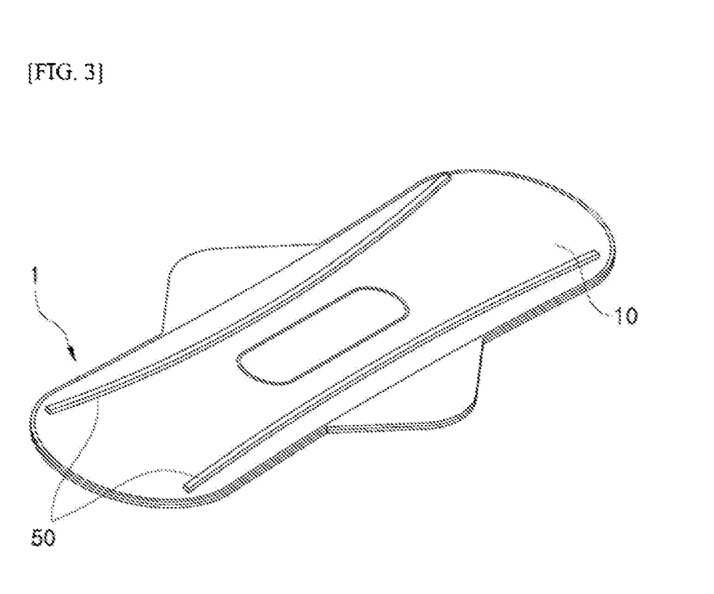
FIG. 3 is a view illustrating a sanitary pad having a leakage preventing protrusion part formed thereon according to an embodiment of the present invention.

FIG. 3 is a view illustrating the sanitary pad 1 having a leakage preventing protrusion part 50 formed thereon according to an embodiment of the present invention.

Referring to FIG. 3, the sanitary pad 1 may further include the leakage preventing protrusion part 50. The leakage preventing protrusion part 50 may be formed to protrude from both sides of the upper sheet 10, the first absorbing sheet 20, and the second absorbing sheet 30 in a longitudinal direction.

The leakage preventing protrusion part 50 may protrude in the shape of a protrusion to prevent menstrual fluid from leaking through wings of the sanitary pad 1. The leakage preventing protrusion part 50 may be formed to protrude and be pressed against the user's skin. Due to being made of pure organic cotton, the leakage preventing protrusion part 50 according to the present invention may not irritate the skin.

Figure 4:
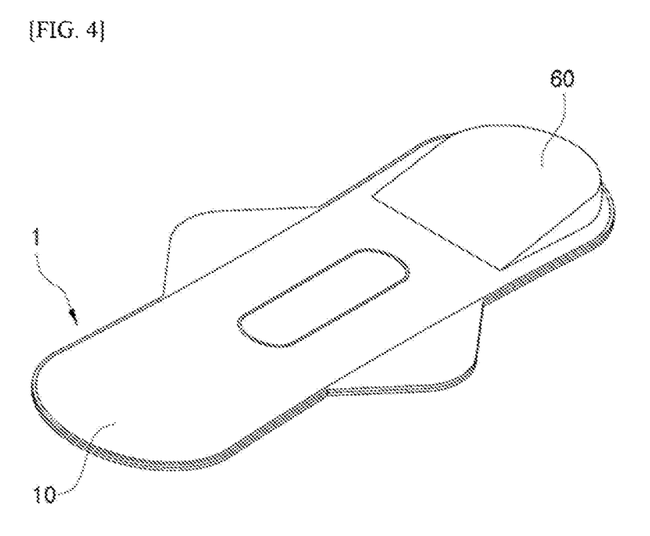
FIGS. 4 to 6 are views illustrating a sanitary pad having a length adjusting part formed thereon according to an embodiment of the present invention.
Figure 5:
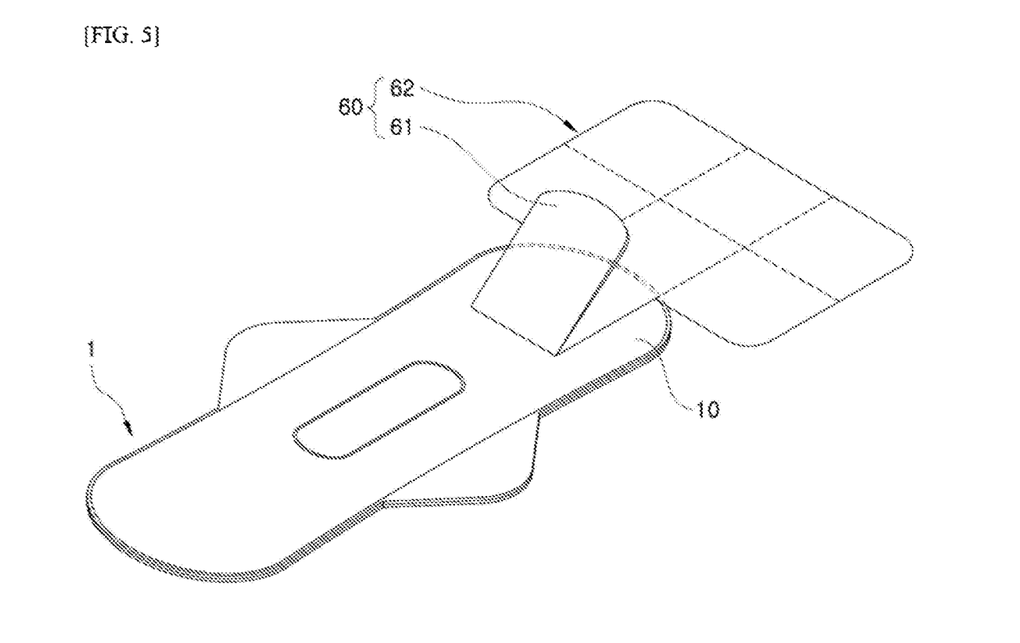
Figure 6:
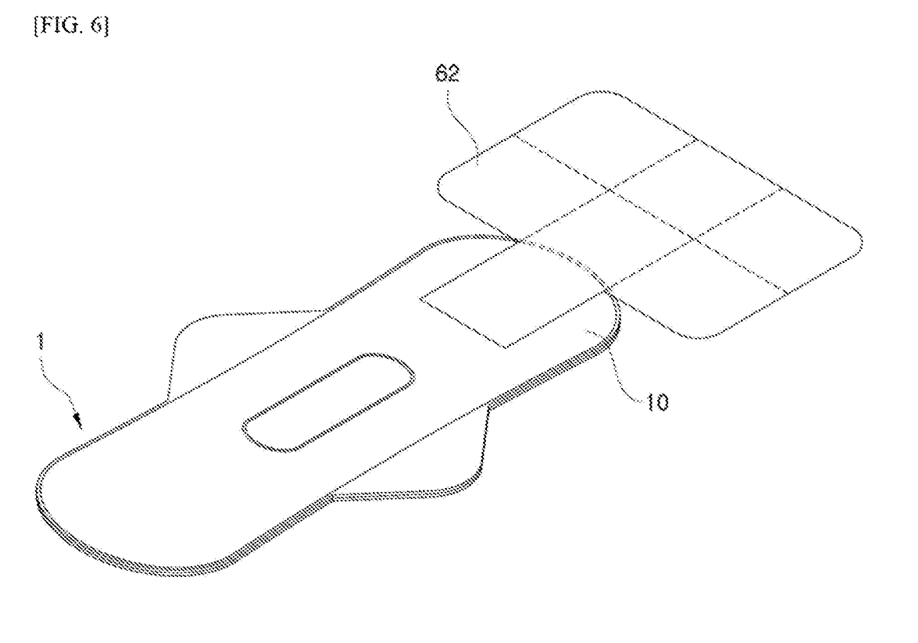

FIGS. 4 to 6 are views illustrating the sanitary pad 1 having a length adjusting part 60 formed thereon according to an embodiment of the present invention.

Referring to FIGS. 4 to 6, the sanitary pad 1 may further include the length adjusting part 60. The length adjusting part 60 may prevent leakage of menstrual fluid while the user is lying down or extend the length of the sanitary pad 1.

The length adjusting part 60 may be disposed at a rear portion of an upper surface of the upper sheet 10. The length adjusting part 60 may be disposed at the rear portion of the upper sheet 10 and formed to gradually protrude more in a rearward direction.

The length adjusting part 60 may include a cover part 61 and an absorbing part 62.

The cover part 61 may have an edge removably connected to the upper sheet 10. An inner surface of the cover part 61 may be formed of a waterproof layer, and an outer surface of the cover part 61 that comes into contact with the skin may be made of pure organic cotton and have a predetermined thickness. That is, due to the waterproof layer, menstrual fluid may only be absorbed into the pure organic cotton of the outer surface of the cover part 61 without being absorbed into the inner surface of the cover part 61.

The absorbing part 62 may be formed to have a predetermined length and a predetermined area that allow extension of the length or width of the sanitary pad 1. The absorbing part 62 may be embedded in a folded state inside the cover part 61 or exposed to the outside and unfolded when the cover part 61 is removed.

Specifically, in a state in which the cover part 61 is not removed from the upper sheet 10 and the circumference of the cover part 61 is connected to the upper sheet 10, the absorbing part 62 may be accommodated in a state of being folded a plurality of times inside the cover part 61. In such a case, the length adjusting part 60 that protrudes from a rear portion (hip side) of the sanitary pad 1 may be pressed against the user's buttocks. For example, in a state in which the length adjusting part 60 protrudes from the upper sheet 10, pressing between the sanitary pad 1 and the buttocks may be enhanced, and leakage of menstrual fluid may be prevented while the user is lying down.

In a case in which the cover part 61 is removed and detached from the upper sheet 10, a folded portion of the absorbing part 62 may be unfolded, and the absorbing part 62 may be unfolded toward an outer side of the rear portion of the upper surface of the upper sheet 10. In a case in which the absorbing part 62 of the length adjusting part 60 is unfolded, the length of the sanitary pad 1 may be increased, or the length and width thereof may be increased. The increased length or width of the sanitary pad 1 may be determined according to the length or width of the absorbing part 62.

In this way, because the size of the sanitary pad 1 is increased by unfolding the absorbing part 62, a single sanitary pad 1 may be used by adjusting the size as necessary, without the need to separately purchase small-sized, medium-sized, and large-sized sanitary pads 1.

Figure 7:
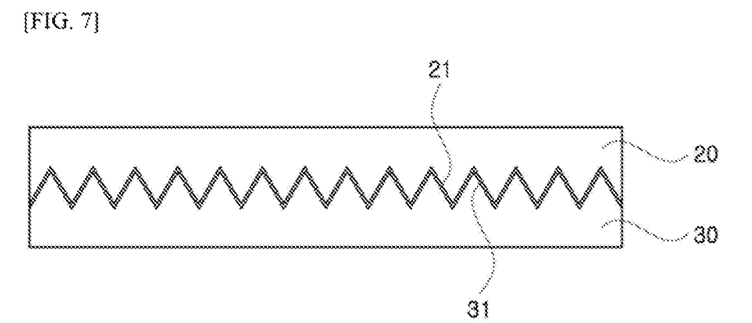
FIGS. 7 and 8 are views illustrating a cross-section of a first absorbing sheet and a second absorbing sheet of a sanitary pad according to an embodiment of the present invention.
Figure 8:
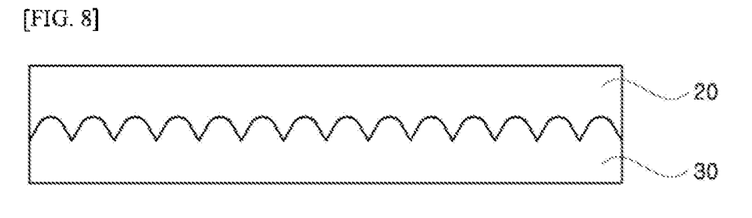

FIGS. 7 and 8 are views illustrating a cross-section of the first absorbing sheet 20 and the second absorbing sheet 30 of the sanitary pad 1 according to an embodiment of the present invention.

Referring to FIGS. 7 and 8, a concave portion 21 may be formed in a lower surface of the first absorbing sheet 20, and a convex portion 31 may be formed on an upper surface of the second absorbing sheet 30.

The first absorbing sheet 20 and the second absorbing sheet 30 may expand due to absorbing the liquid in a state in which the convex portion 31 of the second absorbing sheet 30 is inserted into the concave portion 21 of the first absorbing sheet 20. As illustrated in FIG. 8, the concave portion 21 and the convex portion 31 are pressed against each other as the first absorbing sheet 20 and the second absorbing sheet 30 absorb the liquid, thereby causing the concave portion 21 and the convex portion 31 to expand. Therefore, a fixing force of the first absorbing sheet 20 and the second absorbing sheet 30 may be increased.

According to an embodiment of the present invention, it is possible to provide an eco-friendly sanitary pad that uses pure organic cotton and natural compressed pulp without using superabsorbent polymer.

It is also possible to provide a sanitary pad that uses two absorbing sheets so that an absorption rate and an absorption capacity are improved.

It is also possible to provide a sanitary pad that uses pure organic cotton to increase a cushion feeling and absorption rate and uses natural compressed pulp to increase absorption capacity.

It is also possible to provide a sanitary pad that uses natural compressed pulp manufactured through a chlorine-free bleaching process.

It is also possible to provide a sanitary pad that uses natural compressed pulp which is compressed using only water and heat without using an adhesive.

Typical embodiments of the present invention have been described above in detail, but those of ordinary skill in the art to which the present invention pertains should understand that the embodiments may be modified in various ways within the scope not departing from the present invention. Therefore, the scope of the present invention should be defined by the attached claims and their equivalents rather than being defined merely on the basis of the above embodiments.

DESCRIPTION OF REFERENCE NUMERALS

1: sanitary pad
10: upper sheet
20: first absorbing sheet
21: concave portion
30: second absorbing sheet
31: convex portion
40: waterproof sheet
50: leakage preventing protrusion part
60: length adjusting part
61: cover part
62: absorbing part

What is claimed is:

1. A sanitary pad comprising:
   an upper sheet made of pure organic cotton through which a liquid is permeable;
   a first absorbing sheet disposed below the upper sheet and made of pure organic cotton configured to absorb the liquid, wherein a lower surface of the first absorbing sheet comprises a concave portion;
   a second absorbing sheet disposed below the first absorbing sheet and made of natural compressed pulp configured to absorb the liquid, wherein an upper surface of the second absorbing sheet comprises a convex portion which is inserted into the concave portion;
   a waterproof sheet disposed below the second absorbing sheet and having air permeability; and
   a length adjusting part disposed at a rear portion of an upper surface of the upper sheet,
   wherein the length adjusting part includes
      a cover part, an edge of the cover part in its entire length being removably connected to the upper sheet, and
      an absorbing part, which is embedded in a state of being folded a plurality of times at an inner side of the cover part so that the absorbing part is not exposed to the outside,
   wherein the cover part comprises an inner surface formed of a waterproof layer, and an outer surface made of pure organic cotton in a predetermined thickness, the waterproof layer being configured not to absorb menstrual fluid so that the menstrual fluid is absorbed into the pure organic cotton of the outer surface of the cover part,
   wherein in a state in which the cover part is connected to the upper sheet, the length adjusting part is formed to gradually protrude more in a rearward direction by the absorbing part folded at the inner side of the cover part so that the length adjusting part sticks to buttocks,
   wherein in a state in which the cover part is detached from the upper sheet, a folded portion of the absorbing part is unfolded toward an outer side of the upper sheet, and a length and width of the sanitary pad is increased, and
   wherein the concave portion and the convex portion are configured to be expanded when absorbing the liquid in a state in which the convex portion is inserted into the concave portion such that a fixing force between the first absorbing sheet and the second absorbing sheet is increased.

2. The sanitary pad of claim 1, wherein the second absorbing sheet is manufactured by a chlorine-free bleaching process.

3. The sanitary pad of claim 1, wherein the second absorbing sheet is manufactured by a hydrogen peroxide bleaching process.

* * * * *